United States Patent [19]

Shlenker et al.

[11] Patent Number: 5,128,168

[45] Date of Patent: Jul. 7, 1992

[54] METHOD OF FORMING A MEMBRANE, ESPECIALLY A LATEX MEMBRANE, HAVING A BIOCIDE BARRIER

[75] Inventors: Robin R. T. Shlenker, 2165 E. Alameda, Denver, Colo. 80209; Clive C. Solomons; Jerry D. Plunkett, both of Denver, Colo.; Clayton S. Smith, Golden, Colo.

[73] Assignee: Robin R. T. Shlenker, Denver, Colo.

[21] Appl. No.: 536,773

[22] Filed: Jun. 12, 1990

Related U.S. Application Data

[63] Continuation-in-part of Ser. No. 482,978, Feb. 22, 1990, Pat. No. 5,045,341, which is a continuation-in-part of Ser. No. 246,337, Sep. 19, 1988, Pat. No. 4,935,260, Continuation-in-part of Ser. No. 143,184, Jan. 13, 1988, Pat. No. 4,919,966, which is a continuation-in-part of Ser. No. 74,629, Jul. 17, 1987, Pat. No. 4,771,482.

[51] Int. Cl.⁵ ............................................. A01N 1/02
[52] U.S. Cl. ............................................. 427/2; 2/167; 2/168; 128/844; 523/122; 427/407.1
[58] Field of Search ............... 2/159, 161 R, 167, 168; 128/844; 427/2, 407.1; 604/349, 353; 523/122

[56] References Cited

U.S. PATENT DOCUMENTS

| 4,545,841 | 10/1985 | Jackrel | 156/290 |
| 4,675,347 | 6/1987 | Mochizuki et al. | 106/15.05 X |
| 4,853,978 | 8/1989 | Stockum | 604/292 X |
| 4,867,968 | 9/1989 | Allen | 604/264 X |
| 4,881,277 | 11/1989 | Hogle | 2/169 |
| 4,901,372 | 2/1990 | Pierce | 2/167 |
| 4,930,522 | 6/1990 | Busnel et al. | 128/844 |
| 5,019,096 | 5/1991 | Fox et al. | 427/407.1 X |

OTHER PUBLICATIONS

C. L. Fox Abstracts.

*Primary Examiner*—Michael Lusignan

[57] ABSTRACT

Methods of forming a chemical barrier against the transmission of disease-causing microbes and other harmful agents through a membrane such as latex. In the principal method, a mold or former is coded with a coagulant, which is dried, and then the former is dipped into liquid latex, which is allowed to gel, and then the former is dipped into a solution containing the biocide, and then the former is dipped again into the liquid latex, after which the entire coating on the former is cured. Alternatively, the biocide may be sprayed otherwise applied onto the gelled latex.

25 Claims, No Drawings

METHOD OF FORMING A MEMBRANE, ESPECIALLY A LATEX MEMBRANE, HAVING A BIOCIDE BARRIER

BACKGROUND OF THE INVENTION

This patent application is a continuation-in-part of U.S. patent application Ser. No. 482,978 filed on Feb. 22, 1990 for "Covering Such As A Suit, Glove, Condom Or Sheath Forming A Chemical Barrier Against Harmful Agents And Methods Of Making The same", now U.S. Pat. No. 5,045,341, which in turn is a continuation-in-part of U.S. patent application Ser. No. 246,337 filed on Sep. 19, 1988 for "Covering Such As A Suit, Glove, Condom Or Sheath Forming A Chemical Barrier Against Harmful Agents And Method Of Making The Same", now U.S. Pat. No. 4,935,260, which in turn is a continuation-in-part of U.S. patent application Ser. No. 143,184, filed Jan. 13, 1988 for "Covering Such As A Glove, Condom Or Sheath For Inhibiting The Spread Of Contagious Diseases And Methods Of Making And Using The Same", now U.S. Pat No. 4,919,966, which in turn is a continuation-in-part of U.S. patent application Ser. No. 074,629, filed on Jul. 17, 1987, for "Glove For Inhibiting The Spread Of Contagious Diseases And Method Of Using The Same", now U.S. Pat. No. 4,771,482. All of these applications are owned by the same Applicant. The subject matter of the foregoing patent applications and patent is hereby incorporated by reference.

Latex materials have long been used as gloves and condoms for the purpose of inhibiting the transmission of disease producing microbes and other harmful agents. Both the chemical inertness and the physical density of latex make it difficult for molecules and microbes to pass through the structure of the latex material. Nevertheless, latex materials are known to possess imperfections in the form of pits, pores, and holes, which can facilitate the transmission of such microbes and harmful agents through the latex material.

The present invention relates to the desireable goal of forming a chemical barrier against the transmission of such microbes and other harmful agents through a membrane such as latex.

SUMMARY OF THE INVENTION

The present invention relates to methods of forming a chemical barrier against the transmission of disease-causing microbes and other harmful agents through a membrane such as latex. In the principal method, a mold or former is coated with a coagulant, which is dried, then the former is dipped into liquid latex, which is allowed to gel, then the former is dipped into a solution containing the biocide, and then the former is dipped again into the liquid latex, after which the entire coating on the former is cured. Alternatively, the biocide may be sprayed or otherwise applied onto the gelled latex.

DESCRIPTION OF A PREFERRED EMBODIMENT

The present invention relates to methods of forming a chemical barrier against disease-causing microbes and other harmful agents through a membrane fashioned of latex or another material such as natural skin, natural rubber, solvent cast membranes, elastomers, and polymers that are formed by curing the material from a liquid state. For convenience, the preferred embodiment will be described with reference to a latex material. The latex material may be fashioned as a glove, condom, diaphragm, slipper, overshoe, sterile bands, catheters, latex or plastic tubing, diaphragms, drapes, gut openings, mouthpieces, baby nipples, intra gastric nasal tubes, nasal gastric tubes, kidney shunts, rubber dams for teeth, plastic braces for teeth, sub-clavian vein and artery shunts, colostomy bags, or any other product. Normally these latex products will be adapted for use in juxtaposition to a person's or animal's skin.

As used in the instant patent application, the term "biocide" means that the disease-producing characteristic or harm-causing characteristic is rendered ineffective substantially upon contact or shortly after the microbe or harmful agent contacts the biocide material. A few suitable biocides are believed to be dextran sulphate, nonoxynol-9, benzalkonium, betadyne, gentian violet, acriflavine and acridine dyes, mercurochrome, silver salts, and an extract of blue green algae. Additionally, a very lengthy list of what are believed to be suitable biocides is being filed concurrently with this patent application and forms part of the file wrapper.

Latex products, such as latex gloves and condoms, are conventionally formed by either a single dip or double dip process. A mold or former in the shape of the desired latex product is initially covered with a chemical coagulant, which allows a relatively thick, uniform, continuous layer of latex to be deposited on the former. The coagulant is dried on the former, and then the former is dipped into a vat of liquid latex for an appropriate period of time, whereby a film of latex is picked up on the surface of the former. The latex is allowed to wet gel into a sticky or tacky state, and while in the gel state, is leached in a warm water rinse or bath. The rinse removes the coagulant as well as any residual ammonia or potassium hydroxide which might be present. In order to increase the thickness of latex, the process may be repeated so that a second film of latex is built up integrally over the first layer of latex. Usually the second layer is less thick than the first layer.

A biocide barrier has been incorporated into a latex product in the following experiment. After the first dip of the former into the liquid latex and after the warm water leach in the conventional manner, the former (with the liquid latex in a wet gel state) is dipped into a solution of gentian violet, at a concentration of 0.33% by weight in water. The biocide solution coats the liquid latex. The biocide solution coating is then dried. Thereafter, the former is dipped again into a vat of liquid latex, may be leached again, and then the entire coating on the former is cured by drying.

It appears that the biocide solution acts as a secondary coagulant, and causes the second layer of latex to be relatively thicker than is normally achieved without any biocide solution.

A solution of 1.5% by weight of gentian violet in water has also been used in this process, with slightly less desireable uniformity in thickness of the coatings. Nevertheless, it is believed that the concentrations of up to about 5% by weight of gentian violet in water or water and alcohol with other cosolvents can be advantageously used in the process.

It has been observed that the maximum amount of biocide solution picked-up by the wet gel latex coating the former is about 0.2 grams of solution per gram of latex.

It is believed that the biocide is bonded to and is permanently diffused within the surface of the latex, thereby substantially filling the pores and other imperfections of the latex.

The present invention also contemplates that the biocide solution may be sprayed or otherwise applied to the wet gel latex, instead of being applied by dipping.

Although particular embodiments of the present invention have been described and illustrated herein, it should be recognized that modifications and variations may readily occur to those skilled in the art and that such modifications and variations may be made without departing from the spirit and scope of our invention. Consequently, our invention as claimed below may be practiced otherwise than as specifically described above.

We claim:

1. A method of making a latex material having a biocide barrier comprising the steps of:
    applying a first coating of liquid latex onto a former;
    applying a coating of biocide effective as a coagulant for liquid latex over the first latex coating already on the former; and
    applying a second coating of liquid latex over the biocide and the first latex coating.

2. A method of making a latex material having a biocide barrier according to claim 1 wherein said biocide comprises gentian violet.

3. A method of making a latex material having a biocide barrier according to claim 1 wherein said biocide is selected from the group consisting of dextran sulphate, benzalkonium, betadyne, gentian violet, acriflavine and acridine dyes, mercurochrome, silver salts, and an extract of blue-green algae.

4. A method of making a latex material having a biocide barrier according to claim 1 wherein said biocide is in a solution that coats over the first latex coating and said biocide is in a concentration substantially in the range of 0.10 percent to five percent by weight.

5. A method of making a latex material having a biocide barrier according to claim 1 wherein said biocide is in a solution that coats over the first latex coating and wherein the ration of the mass of the biocide solution coating to the mass of the first latex coating is substantially in the range of 0.05 to 0.3.

6. A method of making a latex material having a biocide barrier according to claim 1 wherein said biocide coating is applied by dipping the first latex coating into a vat of biocide solution.

7. A method of making a latex material having a biocide barrier according to claim 1 wherein said biocide coating is applied by spraying the biocide over the first latex coating.

8. A method of making a latex material having a biocide barrier according to claim 1 wherein said biocide coating is applied over the first latex coating when the first latex coating is in a wet gel state.

9. A method of making a latex material having a biocide barrier according to claim 1 comprising the further step of leaching the first latex coating with water prior to applying the biocide coating, and wherein said biocide coating is applied over the first latex coating when the first latex coating is in a wet gel state.

10. A method of making a latex material having a biocide barrier according to claim 1 wherein said biocide is in a solution that coats over the first latex coating and wherein said solution is substantially completely dried prior to applying the second latex coating.

11. A method of making a latex material having a biocide barrier comprising the steps of:
    applying a coating of biocide effective as a coagulant for liquid latex onto a former; and
    applying a coating of liquid latex over the biocide coating already on the former.

12. A method of making a latex material having a biocide barrier according to claim 1 wherein said biocide comprises gentian violet.

13. A method of making a latex material having a biocide barrier according to claim 11 wherein said biocide is selected from the group consisting of dextran sulphate, benzalkonium, betadyne, gentian violet, acriflavine and acridine dyes, mercurochrome, silver salts, and an extract of blue-green algae.

14. A method of making a latex material having a biocide barrier according to claim 11 wherein said biocide is in a solution in a concentration substantially in the range of 0.10 percent to five percent by weight.

15. A method of making a latex material having a biocide barrier according to claim 11 wherein said biocide is in a solution and wherein the ration of the mass of the biocide solution coating to the mass of the latex coating is substantially in the range of 0.05 to 0.3.

16. A method of making a latex material having a biocide barrier comprising the steps of:
    applying a first coating of liquid latex onto a former;
    applying a coating of biocide effective as a coagulant for liquid latex selected from the group consisting of dextran sulphate, benzalkonium, betadyne, gentian violet, acriflavine and acridine dyes, mercurochrome, silver salts, and an extract of blue-green algae, said biocide in solution in a concentration substantially in the range of 0.10 percent to five percent by weight, over the first latex coating already on the former such that the ratio of the mass of the biocide solution coating to the mass of the first latex coating is substantially in the range of 0.05 to 0.3; and
    applying a second coating of liquid latex over the biocide and the first latex coating.

17. A method of making a latex material having a biocide barrier according to claim 16 wherein said biocide coating is applied by dipping the first latex coating into a vat of biocide solution.

18. A method of making a latex material having a biocide barrier according to claim 16 wherein said biocide coating is applied by spraying the biocide over the first latex coating.

19. A method of making a latex material having a biocide barrier according to claim 16 wherein said biocide coating is applied over the first latex coating when the first latex coating is in a wet gel state.

20. A method of making a latex material having a biocide barrier according to claim 16 comprising the further step of leaching the first latex coating with water prior to applying the biocide coating, and wherein said biocide coating is applied over the first latex coating when the first latex coating is in a wet gel state.

21. A method of making a latex material having a biocide barrier according to claim 16 wherein said biocide is in a solution that coats over the first latex coating and wherein said solution is substantially completely dried prior to applying the second latex coating.

22. A method of making a latex material having a biocide barrier comprising the steps of:

applying a coating of biocide effective as a coagulant for liquid latex selected from the group consisting of dextran sulphate. benzalkonium. betadyne, gentian violet. acriflavine and acridine dyes, mercurochrome, silver salts, and an extract of blue-green algae, said biocide in solution in a concentration substantially in the range of 0.10 percent to five percent by weight, onto a former; and applying a coating of liquid latex over the biocide coating already on the former such that the ratio of mass of the biocide solution coating to the mass of the latex coating is substantially in the range of 0.05 to 0.3.

23. A method of making a latex material having a biocide barrier according to claim 22 wherein said biocide coating is applied by dipping the former into a vat of biocide solution.

24. A method of making a latex material having a biocide barrier according to claim 22 wherein said biocide coating is applied by spraying the biocide over the former.

25. A method of making a latex material having a biocide barrier according to claim 22 wherein said biocide is in a solution that coats over the former and wherein said solution is substantially completely dried prior to applying the latex coating.

* * * * *